United States Patent [19]

Babcock et al.

[11] 4,227,002

[45] Oct. 7, 1980

[54] HALO-A-23187 DERIVATIVES

[75] Inventors: Donner F. Babcock, Madison, Wis.; Charles M. Deber, Toronto, Canada; Manuel Debono; R. Michael Molloy, both of Indianapolis, Ind.; Douglas R. Pfeiffer, Austin, Minn.

[73] Assignee: Eli Lilly and Company, Indianapolis, Ind.

[21] Appl. No.: 950,487

[22] Filed: Oct. 11, 1978

[51] Int. Cl.$^2$ .................. C07D 493/10; A61K 31/42
[52] U.S. Cl. ................... 548/216; 548/104; 424/272; 252/184
[58] Field of Search ................. 260/307 D; 548/216, 548/104

[56]   References Cited
U.S. PATENT DOCUMENTS

| | | | |
|---|---|---|---|
| 3,873,715 | 3/1975 | Pressman | 424/283 |
| 3,923,823 | 10/1975 | Gale et al. | 260/307 D |
| 3,944,573 | 3/1976 | Wostley | 424/285 |
| 3,960,667 | 6/1976 | Gale et al. | 195/80 R |

OTHER PUBLICATIONS

Chaney et al., J. Antibiotics, 29, 424–427 (1976).

*Primary Examiner*—Mark L. Berch
*Attorney, Agent, or Firm*—Nancy J. Harrison; Arthur R. Whale

[57]   ABSTRACT

Halo-A-23187 derivatives, prepared by reaction of antibiotic A-23187 with an N-halo-type halogenating agent, and salts thereof, which are (1) useful biochemical tools for the study of transport of ions in cellular systems, (2) useful chemical tools for removal and recovery of ions, and (3) potential cardiotonic agents.

7 Claims, No Drawings

HALO-A-23187 DERIVATIVES

BACKGROUND OF THE INVENTION

Field of the Invention

Antibiotic A-23187 is a unique polyether antibiotic having the following structure

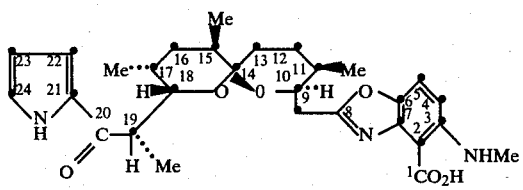

The numbering system used herein for A-23187 is that proposed by M. O. Chaney, Noel D. Jones and Manuel Debono in J. Antibiotics 29 (4), 424–427 (1976).

In Westley's review on polyether antibiotics, he classifies ionophores by chemical structure [see J. W. Westley in "Advances in Applied Microbiology," Vol. 22, D. Perlman, Ed., Academic Press, New York, N.Y., 1977, pages 177–223]. Using Westley's classification, there are four types of ionophore antibiotics: (1) polyethers; (2) peptides; (3) cyclodepsipeptides; and (4) macrotetrolides. Within the polyether subclass, there are four subgroups: (1a) monovalent polyethers (e.g., monensin, nigericin); (1b) monovalent monoglycoside polyethers (e.g., dianemycin); (2a) divalent polyethers (e.g., lasalocid, lysocellin) and (2b) divalent pyrrole ethers (e.g., antibiotic A-23187). To date, antibiotic A-23187 is the only known member of this last group.

Ionophore A-23187 has proven to be a powerful and unique research tool to investigate $Ca^{2+}$-dependent control mechanisms in a large variety of cellular systems. Calcium ($Ca^{2+}$) ion is widely recognized as an intracellular "second messenger" [H. Rasmussen and D. P. B. Goodman, Physiological Reviews 57 (3), 421–509 (1977)]. The mechanisms by which $Ca^{2+}$ controls cellular excitation phenomena appear similar to, and linked to, control by cyclic nucleotides and prostaglandins.

Of approximately 100 known, naturally occurring ionophores, A-23187 is one of three which are able to transport divalent cations significantly (the other two being lasalocid and beauvericin). A-23187 is the only ionophore substantially selective for the transport of divalent over monovalent cations [For a recent review, see D. R. Pfeiffer, R. W. Taylor and H. A. Lardy, Am. N.Y. Acad, Sci 307, 402–423 (1978)].

Despite this unique utility, A-23187 is not an ideal $Ca^{2+}$ ionophore from a physiological viewpoint. It transports $Mg^{2+}$ with a similar efficiency to $Ca^{2+}$, and its discrimination for divalent over monovalent cations is not complete [D. R. Pfeiffer and H. A. Lardy, Biochemistry 15, 935 (1976)].

The Prior Art

Halo derivatives of the polyether antibiotics lasalocid A (antibiotic X-537A; U.S. Pat. No. 3,873,715) and iso-lasalocid A (U.S. Pat. No. 3,944,573) are known. The complex structure of antibiotic A-23187, however, precludes any a priori prediction of the site(s) of halogenation.

BRIEF SUMMARY OF THE INVENTION

We have discovered specific halo derivatives of A-23187 having unique ionophorous activity. The compounds of our invention are selected from a group consisting of the following:

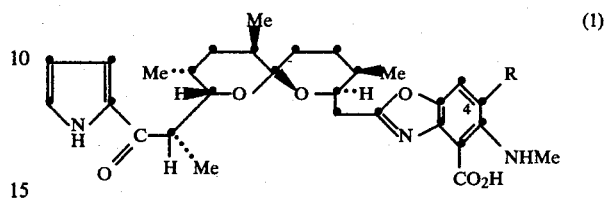

wherein R is bromine or chlorine;

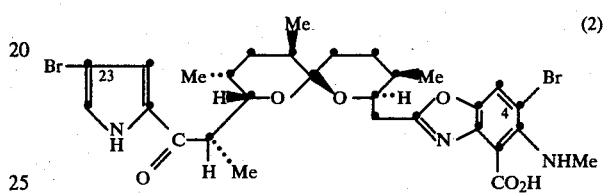

and

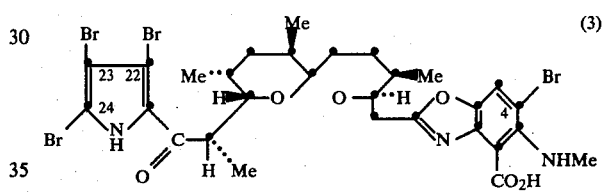

and the salts of (1), (2) and (3). As is the case with antibiotic A-23187, when the compounds of this invention form salts with divalent cations, these salts contain two molecules of A-23187 derivative per molecule of metal ion. Such salts are frequently referred to as complexes.

Chemical names for the compounds of formulas (1), (2), and (3) are as follows:

| Compounds of Formula | Name |
|---|---|
| (1) | 6-bromo(or chloro)-5-(methylamino)-2-[[3β,9α,-11β-trimethyl-8-[1α-methyl-2-oxo-2-(1H-pyrrol-2-yl)ethyl]-1,7-dioxaspiro[5.5]undec-2β-yl]methyl]-4-benzoxazolecarboxylic acid; |
| (2) | 6-bromo-5-(methylamino)-2-[[3β,9α,11β-trimethyl-8-[1α-methyl-2-oxo-2-(4-bromo-1H-pyrrol-2-yl)ethyl]-1,7-dioxaspiro[5.5]undec-2β-yl]methyl]-4-benzoxazolecarboxylic acid; and |
| (3) | 6-bromo-5-(methylamino)-2-[[3β,9α,11β-trimethyl-8-[1α-methyl-2-oxo-2-(3,4,5-tribromo-1H-pyrrol-2-yl)ethyl]-1,7-dioxaspiro[5.5]undec-2β-yl]methyl]-4-benzoxazolecarboxylic acid. |

For convenience herein, these compounds will be identified as A-23187 derivatives, i.e., as follows:

| Compounds of Formula | Name |
|---|---|
| (1) | 4-bromo-A-23187 and 4-chloro-A-23187 |
| (2) | 4,23-dibromo-A-23187 |

| Compounds of Formula | Name |
|---|---|
| (3) | 4,22,23,24-tetrabromo-A-23187 |

The compounds of the present invention are prepared by reacting A-23187 (as a dimeric complex with a divalent cation) with an appropriate N-halo-type halogenation agent. N-chlorosuccinimide (NCS) and N-bromosuccinimide (NBS) are especially useful in the preparation of the compounds of this invention.

The compounds of this invention have a unique effect on ion transport and are, therefore, new tools for the study of cation binding and transport selectivity patterns for divalent and monovalent cations of biochemical importance. Such tools are important, for example, for the study of (1) mechanisms regulating intracellular ionic distributions and concentrations and (2) the involvement of the intracellular ionic environment in the regulation of cellular functions, especially those of a contractile or secretory nature. In one aspect of this utility, the compounds are potential inotropic agents.

Furthermore, the compounds of this invention provide new tools for the selective chemical removal of particular cations.

DETAILED DESCRIPTION OF THE INVENTION

The compounds of this invention are prepared from antibiotic A-23187. Antibiotic A-23187 can be prepared by culturing the microorganism *Streptomyces chartreusis* Calhoun and Johnson NRRL 3882 and then isolating antibiotic A-23187 as described by Gale et al. in U.S. Pat. Nos. 3,923,823 and 3,960,667.

The compounds of this invention are prepared from antibiotic A-23187 by reaction with an N-halo-type halogenation agent, such as N-bromosuccinimide and N-chlorosuccinimide. Generally, a dimeric complex of A-23187 with a divalent cation is used, thereby preparing the desired compound of this invention as the corresponding divalent salt. These dimeric complexes can be represented by the abbreviation "$A_2$-M" wherein A represents the A-23187 moiety and M represents the metal cation. The free acid form of the compounds of this invention can then be prepared from the complex form by standard procedures, such as dissolving the complex in an appropriate organic solvent and washing the solvent with an acidic solution. Other salts can be prepared from the free acid by conventional chemical methods.

The compounds of formulas (1), (2), and (3) and the salts of these compounds are included within our invention. The salts are useful for solubilizing cationic species in nonaqueous solvents. Among these salts, salts which are "pharmaceutically acceptable" are a preferred group since they are especially amenable for involvement in studies of the transport of ions in cellular systems and as potential cardiotonic agents. "Pharmaceutically acceptable" salts are those salts in which the toxicity of the compound as a whole toward warm-blooded animals is not increased relative to the non-salt form.

Representative and suitable salts of the compounds of formulas (1), (2), and (3) include those salts formed with divalent and monovalent cations. Alkaline-earth-metal salts, alkali-metal salts and transition-metal salts are among the suitable salts contemplated by this invention. Typical useful divalent cations for salt (complex) formation include magnesium, calcium, manganese, cadmium, barium, iron, zinc, lead, mercury and the like. Typical monovalent cations include sodium, potassium, lithium, and the like.

The compounds of this invention are useful antibacterial agents. In this aspect, these compounds may be used in the same manner in which the parent antibiotic is used, as described in U.S. Pat. No. 3,923,823. A bioassay for the antibacterial activity of A-23187 has been described by J. E. Westhead in *Antimicrobial Agents and Chemotherapy* 11 (5), 916–918 (1977). The test organism for this bioassay is *Staphylococcus aureus* (H-Heatley strain, NRRL B-314). Table I summarizes the results of typical compounds of this invention using this bioassay.

TABLE I

| Compound | Bioassay (mcg/ml) |
|---|---|
| 4-chloro-A-23187 (free acid) | 298 |
| 4-bromo-A-23187 (free acid) | 835 |
| 4,23-dibromo-A-23187 (free acid) | 940 |
| 4,22,23,24-tetrabromo-A-23187 (free acid) | 585 |
| A-23187 (free acid) | 1060 |

The compounds of the present invention are, in general, less toxic than the parent antibiotic. Table II summarizes the acute toxicities of representative compounds in mice, expressed as $LD_{50}$, when the compounds are administered intraperitoneally.

TABLE II

| Compound | $LD_{50}$ (mg/kg × 1) |
|---|---|
| 4-chloro-A-23187 (Mg complex) | 29.8 |
| 4-chloro-A-23187 (free acid) | 10.5 |
| 4-bromo-A-23187 (Mg complex) | 18.75 |
| 4-bromo-A-23187 (free acid) | 11.9 |
| A-23187 (free acid) | 5.8 |

In a more important aspect, the compounds of this invention exhibit ion-binding and ion-transport properties and are, therefore, ionophores (ion-bearers) (see B. C. Pressman, Alkali Metal Chelators—The Ionophores, in "Inorganic Biochemistry," Volume 1, G. L. Eichhorn, Elsevier, 1973). Such compounds can be used when the selective removal of a particular cation is desired. Examples of such uses include the removal and recovery of silver ions from solutions in photography, the removal of toxic cations from industrial waste streams before such streams are discharged to the environment, and deionization of sea water. A compound of this invention can be used as one component of an ion-specific electrode (see O. Kedem, et al., U.S. Pat. No. 3,753,887). These compounds alter the cation permeability of both natural and artificial membranes. A compound of this invention can be used, therefore, as a component in a membrane used for the selective transport of cations against a concentration gradient. One potential application of this property is in recovery of heavy and precious metals on a commercial basis [see E.

L. Cussler, D. F. Evans, and Sister M. A. Matesick, *Science* 172, 377 (1971)].

The fact that the compounds of this invention are useful as biochemical tools in the study of mechanisms regulating intracellular ionic distributions and concentrations is supported by tests which indicate a pattern of activity similar to that of the parent antibiotic A-23187. For example, the affinity of 4-bromo-A-23187 (free acid) for $Ca^{2+}$ and $Mg^{2+}$ was determined by the two-phase extraction technique, using aqueous phases of varying pH [see Pfeiffer and Lardy, *Biochem.* 15, 935 (1976) for details[. The results of these determinations are summarized in Table III.

TABLE III

| Compound | $pK_{Mg}$ | $pK_{Ca}$ |
|---|---|---|
| 4-bromo-A-23187 | 6.26 | 5.91 |
| A-23187 | 6.89 | 6.51 |

As the results in Table III indicate, 4-bromo-A-23187 has a higher affinity for both cations than does the parent antibiotic. The relative affinities ($Ca^{2+}/Mg^{2+}$) of 4-bromo-A-23187 and A-23187 are, however, similar.

The compounds of this invention affect ion transport with altered selectivities compared to the parent compound. In studies with 4-bromo-A-23187, for example, it was found that $Mg^{++}$ is much less effective in inhibiting the influx of $Ca^{++}$ into bovine spermatozoa induced by 4-bromo-A-23187 than it is in inhibiting influx of $Ca^{++}$ induced by a comparable dosage of A-23187.

| | $Ca^{++}$ Influx Induced By | |
|---|---|---|
| | A-23187 | 4-bromo-A-23187 |
| $[Mg^{++}]/[Ca^{++}]$ | (nmole $Ca^{++}$ min × mg protein) | |
| 0 | 3.5 | 3.4 |
| 5 | 2.0 | — |
| 10 | 1.2 | — |
| 20 | 0.5 | 3.4 |
| 40 | — | 3.4 |
| 80 | — | 0.5 |

Antibiotic A-23187 activates the motility and induces the acrosome reaction of mammalian sperm [D. F. Babcock, N. L. First and H. A. Lardy, *J. Biol. Chem.* 251, 3881–3886 (1976); and J. P. Singh, D. F. Babcock and H. A. Lardy, *Biochem. J* 172, 549–556 (1978)]. Activation of motility and induction of the acrosome reaction are alterations apparently required for fertilization.

The compounds of this invention also activate motility and induce the acrosome reaction of mammalian sperm. In one aspect of this invention, therefore, the halo-A-23187 derivatives of this invention may be useful to either promote or inhibit fertilization.

For example, it may be feasible to transfer embryos derived from gametes of livestock with desirable genetic makeups to recipient females of lesser genetic value. Production of such embryos in vitro may be promoted by treatment of the sperm or eggs, or both, with the agents of this invention. Similarly, certain cases of human infertility might be alleviated by treatment of the spermatozoa of the prospective father with these agents, prior to artificial insemination.

Table IV summarizes the effect of an illustrative compound of this invention on mammalian sperm motility and acrosome reaction.

TABLE IV

| Treatment | Bovine Sperum Motility Index | Cuinea Pig Sperm Time Until Acrosome Reaction (min) |
|---|---|---|
| None | 2 | 110 |
| A-23187 | 4 | 30 |
| 4-bromo-A-23187 | 5 | 30 |

In yet another aspect, the compounds of this invention are active as inhibitors of the enzyme ATPase. ATPase, an alkali-metal-sensitive enzyme found in cell membranes, is involved in the energy necessary for active transport. "Active transport" refers to the energy-requiring series of operations whereby intracellular and extracellular fluids maintain their compositions. Inhibitors of ATPase reduce the energy required for active transport. Table V summarizes the results of in vitro tests measuring inhibition of cation transport ATPase in liver mitochondria [measured as half effective concentration (Ic 50) in mcg/ml].

TABLE V

| | ATPase Induced By | |
|---|---|---|
| Compound | $K^+$ monazomycin | $CaCl_2$ |
| 4-chloro-A-23187 (free acid) | 0.2 | 10 |
| 4-bromo-A-23187 (free acid) | 0.3 | 0.9 |
| 4,23-dibromo-A-23187 (free acid) | 0.5 | 0.9 |
| A-23187 (free acid) | 0.5 | 0.5 |

The compounds of this invention are also potential cardiotonic agents. In tests using isolated guinea-pig atria, for example, these compounds increased cardiac contractility. Response to this test is expressed as a percentage of the maximal contractile tension that could be elicited by a challenge dose of norepinephrine ($10^{-4}$ M). For a more detailed description of this test, see U.S. Pat. No. 3,985,893. In this test, 4-bromo-A-23187 free acid and its $Mg^{++}$ salt, each at a $10^{-5}$ molar concentration, produced mean increases in contractile tension of 48 and 59 percent, respectively.

In order to illustrate more fully the operation of this invention the following examples are provided.

EXAMPLE 1

Preparation of 4-Chloro-A-23187 Magnesium Complex

A-23187 $Mg^{++}$ complex (5.34 g, 5.0 mmol) was dissolved in $CCl_4$ (1 L.). To this solution was added pyridine (15 ml, anhydrous), followed by 1,3-N,N-dichloro-5,5-dimethylhydantoin (1.97 g, 10 mmol). The reaction mixture was heated to 60° for 4 hrs in the dark and then cooled and concentrated in vacuo to near dryness to give a yellow syrup. This yellow syrup was diluted with $CHCl_3$ (1 L.) and was washed twice with a 2% solution of sodium sulfite and twice with water. The chloroform extract was dried over sodium sulfate overnight in the dark. Removal of the volatiles and crystallization of the foam from methanol gave 4.06 g (71% yield) of crystalline product, melting at 313°–17°.

$[\alpha]_D^{25} + 331.7°$ (c 0.97, $CH_3OH$); $\lambda_{max}$ ($CH_3OH$) 228 ($\epsilon$45,000), 304 ($\epsilon$34,400), and 340 nm (sh., $\epsilon$10,800); $^1H$ NMR ($CDCl_3$; 100 MHz, 6–8 ppm region) pyrrole protons: 6.26 (m), 7.00 (m), and 7.39 ppm (m); benzoxazole proton: 7.60 ppm (s).

Analysis. Calcd for $C_{58}H_{70}Cl_2N_6O_{12}\cdot Mg$: C, 61.18; H, 6.20; N, 7.38; Cl, 6.22: Found: C, 61.33; H, 6.15; N, 7.17; Cl, 6.47.

EXAMPLE 2

Preparation of 4-Chloro-A-23187 Free Acid

4-Chloro-A-23187 magnesium complex (100 mg, 0.087 mmol), prepared as described in Example 1, was dissolved in $CHCl_3$ (50 ml). This solution was washed twice with 0.1 N HCl and twice with water. The chloroform was then dried over $Na_2SO_4$ and concentrated in vacuo to give 93 mg of pure 4-chloro-A-23187 free acid as a foam (95% yield):

$[\alpha]_D^{25}+30.4$ (c 4.0, $CH_3OH$); $\lambda_{max}$ ($CH_3OH$) 226 ($\epsilon$19,400) and 289 nm ($\epsilon$14,393); $^1H$ NMR ($CDCl_3$, 100 MHz, 6-8 ppm region) pyrrole protons: 6.25 (m), 6.92 (m), and 7.06 ppm (m); benzoxazole proton: 7.72 ppm (s).

Analysis. Calcd for $C_{29}H_{36}ClN_3O_6$: C, 62.41; H, 6.50; N, 7.53; Cl, 6.35: Found: C, 62.18; H, 6.32; N, 7.23; Cl, 6.61.

EXAMPLE 3

Preparation of 4-Bromo-A-23187 Magnesium Complex

A-23187 $Mg^{++}$ complex (1068 mg, 1.0 mmol) was added to anhydrous $CCl_4$ (100 ml). After solution, a total of 400 mg (4.0 mmol) of succinimide was added. With rapid stirring 720 mg (4.0 mmol) of N-bromosuccinimide was added in one portion. After stirring for 4-5 hrs in the dark at room temperature, the yellow reaction mixture was filtered. The solids were washed thoroughly with $CCl_4$. The filtrate was diluted with 300 ml of $CHCl_3$ and washed twice with a 2% solution of sodium sulfite and twice with water. The organic solution was then dried over $Na_2SO_4$ overnight. Removal of volatiles in vacuo and crystallization of the foamy residue from MeOH yielded 1.13 g of crystalline 4-bromo-A-23187 magnesium complex, melting at 316°-319° (92% yield).

$[\alpha]_D^{25}+287.2$ (c 0.188, $CH_3OH$); $\lambda_{max}$ (MeOH) 231 ($\epsilon$39,369), 305 ($\epsilon$32,000), and 340 nm (sh, $\epsilon$10,000); $^1H$ NMR ($CDCl_3$, 100 MHz, 6-8 ppm region) pyrrole protons: 6.25 (m), 7.00 (m), and 7.37 ppm (m); benzoxazole proton: 7.80 ppm (s).

Analysis. Calcd for $C_{58}H_{70}Br_2N_6O_{12}\cdot Mg$: C, 56.76; H, 5.74; N, 6.84; Br, 13.02: Found: C, 56.47; H, 5.93; N, 6.78; Br, 14.48.

Field desorption MS: m/e=1224 ($^{79}Br$).

EXAMPLE 4

Preparation of 4-Bromo-A-23187 Free Acid

4-Bromo-A-23187 magnesium complex (858 mg, 0.7 mmol), prepared as described in Example 3, was dissolved in methylene chloride (400 ml). This solution was washed twice with 0.1 N HCl solution, once with water, and then was dried over $Na_2SO_4$ overnight to give 809 mg of 4-bromo-A-23187 free acid as a yellow foam (96% yield).

$[\alpha]_D^{25}+26.9°$ (c 3.3, $CH_3OH$); $\lambda_{max}$ ($CH_3OH$) 227 ($\epsilon$21,000), 290 ($\epsilon$15,562) and 340 nm (sh, $\epsilon$4,000); $^1H$ NMR ($CDCl_3$, 100 MHz, 6-8 ppm region) pyrrole protons: 6.25 (m), 6.93 (m), and 7.06 ppm (m); benzoxazole proton: 7.93 ppm (s).

Analysis. Calcd for $C_{29}H_{36}BrN_3O_6$: C, 57.81; H, 6.02; N, 6.97; Br, 13.26: Found: C, 57.55; H, 5.77; N, 6.77; Br, 13.52.

EXAMPLE 5

Preparation of 4,23-Dibromo-A-23187 Free Acid and 4,22,23,24-Tetrabromo-A-23187 Free Acid A-23187 magnesium complex (107 mg, 0.1 mmol) was dissolved in $CCl_4$ (10 ml). To this solution was added succinimide (80 mg, 0.8 mmol) and then N-bromosuccinimide (144 mg, 0.8 mmol). After being stirred 54 hours at room temperature in the dark, the yellow reaction mixture was cooled to 5° and filtered, washing the solids thoroughly with $CCl_4$. The filtrate was concentrated in vacuo to dryness. The resulting residue was redissolved in $CHCl_3$; the $CHCl_3$ solution was washed sequentially with 2% $Na_2SO_3$ solution and water, was dried over $Na_2SO_4$ overnight at 5° in the dark, and then was concentrated in vacuo to dryness to give 128 mg of a yellow foam. Chromatography of this material over 50 g of citric-acid-impregnated silica gel (CASG, Woelm, 70-150 mesh), eluting with $CHCl_3$, gave 27 mg of pure 4,22,23,24-tetrabromo-A23187 free acid (16% yield): $R_f=0.35$ ($CHCl_3:CH_3OH$, 95:5, citric-acid-sprayed silica-gel TLC plates);

$[\alpha]_D^{25}+35.6°$ (c 2, $CH_3OH$); $\lambda_{max}$ ($CH_3OH$) 299 ($\epsilon$14,149) sh; and 230 nm ($\epsilon$6600); $^1H$ NMR ($CDCl_3$, 100 MHz, 6-8 ppm region) pyrrole protons: (none); benzoxazole proton: 7.93 ppm (s); MS m/e 835, 791 (-$CO_2$), 552 (q), 396 (d), 328 (q), 240 (d).

Further elution of the CASG column with $CHCl_3$ gave 4,23-dibromo-A23187 free acid ($R_f$ 0.30 in TLC system described for tetrabromo-derivative) as a foam weighing 32 mg (24% yield):

$[\alpha]_D^{25}+47.7°$ (c 2, $CH_3OH$); $\lambda_{max}$ ($CH_3OH$) 208 ($\epsilon$14,091) and 293 nm ($\epsilon$8400); $^1H$ NMR ($CDCl_3$, 100 MHz, 6-8 ppm region) pyrrole protons: 6.90 (br s) and 7.06 ppm (br s); $D_2O$ exchange gave doublets (J=1.5 cps); benzoxazole proton: 7.93 ppm (s). Anal. Calcd for $C_{29}H_{35}Br_2N_3O_6$: C, 51.12; H, 5.18; N, 6.17; Br, 23.45. Found: C, 51.42; H, 5.32; N, 5.93; Br, 23.40.

We claim:

1. A compound selected from a group consisting of compounds having the following formulas:

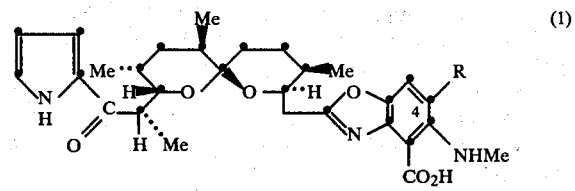
(1)

wherein R is bromine or chlorine;

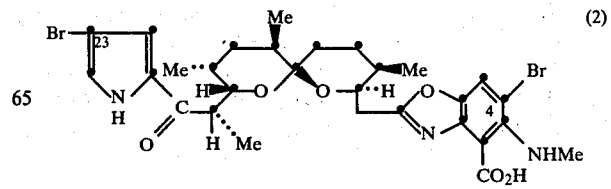
(2)

-continued

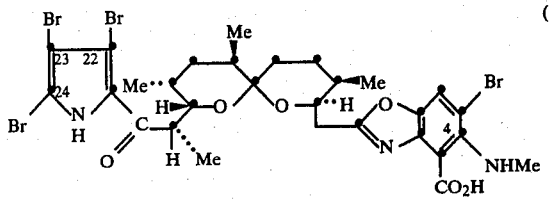
(3)

and the pharmaceutically acceptable cationic salts of (1), (2) and (3).

2. A compound of claim 1 having formula (1) and the pharmaceutically acceptable cationic salts of (1).

3. A compound of claim 1 having formula (3) and the pharmaceutically acceptable cationic salts of (3).

4. A compound of claim 2 wherein R is bromine.

5. The compound of claim 4 which is 4-bromo-A-23187 magnesium salt.

6. A compound of claim 2 wherein R is chlorine.

7. A compound of claim 1 having formula (2) and the pharmaceutically acceptable cationic salts of (2).

* * * * *

UNITED STATES PATENT AND TRADEMARK OFFICE
CERTIFICATE OF CORRECTION

PATENT NO. : 4,227,002  Page 1 of 2
DATED : October 7, 1980
INVENTOR(S) : Donner F. Babcock et al.

It is certified that error appears in the above-identified patent and that said Letters Patent are hereby corrected as shown below:

Column 2, lines 30-33, formula (3), that portion of the structural formula reading

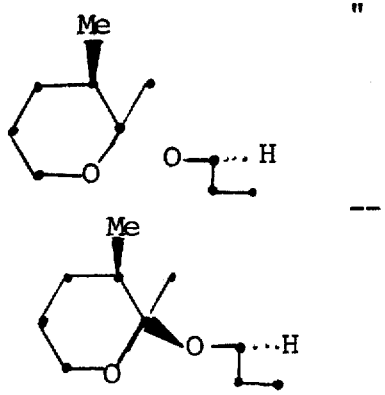

should read --

Column 5, line 12, "details[." should read -- details]. --.

UNITED STATES PATENT AND TRADEMARK OFFICE
CERTIFICATE OF CORRECTION

PATENT NO. : 4,227,002
DATED : October 7, 1980
INVENTOR(S) : Donner F. Babcock et al.

It is certified that error appears in the above-identified patent and that said Letters Patent are hereby corrected as shown below:

Column 9, lines 8-10, formula (3), that portion of the structural formula reading " 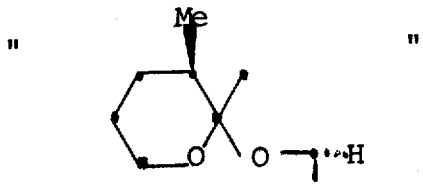 "

should read -- 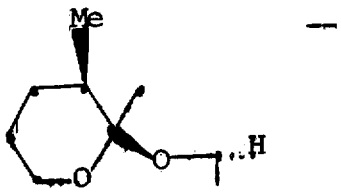 --

Signed and Sealed this

*Thirtieth* Day of *June 1981*

[SEAL]

Attest:

RENE D. TEGTMEYER

*Attesting Officer*     *Acting Commissioner of Patents and Trademarks*